(12) United States Patent
Schultz

(10) Patent No.: US 9,308,137 B2
(45) Date of Patent: Apr. 12, 2016

(54) TRANSITIONAL ABSORBENT PAD AND PANTILINER

(71) Applicant: Kimberly-Clark Worldwide, Inc., Neenah, WI (US)

(72) Inventor: Cheri Lee Schultz, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 212 days.

(21) Appl. No.: 13/852,438

(22) Filed: Mar. 28, 2013

(65) Prior Publication Data

US 2014/0296819 A1    Oct. 2, 2014

(51) Int. Cl.
*A61F 13/15* (2006.01)
*A61F 13/532* (2006.01)
A61F 13/551 (2006.01)
A61F 13/47 (2006.01)

(52) U.S. Cl.
CPC ......... *A61F 13/5323* (2013.01); *A61F 13/4704* (2013.01); *A61F 13/47* (2013.01); *A61F 13/5513* (2013.01); *A61F 13/5519* (2013.01); *A61F 13/55145* (2013.01)

(58) Field of Classification Search
CPC ..... A61F 13/47; A61F 13/45; A61F 13/5513; A61F 13/55145; A61F 13/5519
USPC ...................... 604/385.01, 378, 380, 385.201
See application file for complete search history.

(56) References Cited

U.S. PATENT DOCUMENTS

| | | |
|---|---|---|
| D247,372 S | 2/1978 | Whitehead |
| D254,099 S | 2/1980 | Richards |
| D272,190 S | 1/1984 | Sneider |
| D276,073 S | 10/1984 | Whitehead |
| D276,183 S | 10/1984 | Whitehead |
| 4,758,241 A | 7/1988 | Papajohn |
| D350,200 S | 8/1994 | Gerhartl |
| 5,514,104 A | 5/1996 | Cole et al. |
| D393,712 S | 4/1998 | Clay |
| D434,145 S | 11/2000 | Sugahara |
| D445,179 S | 7/2001 | King |
| 6,352,529 B1 | 3/2002 | Kreutz et al. |
| D460,176 S | 7/2002 | Carlucci et al. |
| D482,781 S | 11/2003 | Glaug et al. |
| D482,782 S | 11/2003 | Glaug et al. |
| D482,783 S | 11/2003 | Glaug et al. |
| D483,117 S | 12/2003 | Glaug et al. |
| D483,119 S | 12/2003 | Glaug et al. |
| 6,844,482 B2 | 1/2005 | Eliasson |
| D506,254 S | 6/2005 | Carlucci et al. |

(Continued)

FOREIGN PATENT DOCUMENTS

WO    WO 00/71067 A1    11/2000

*Primary Examiner* — Jacqueline Stephens
(74) *Attorney, Agent, or Firm* — Kimberly-Clark Worldwide, Inc.

(57) ABSTRACT

An array of personal care absorbent articles includes a menstrual absorbent article having a perimeter, a first transverse midline, a first minimum width line, and a menstrual absorbent layer having a menstrual absorbent shape, the perimeter defining a first article shape and a first article size. The array also includes an incontinence absorbent article having a perimeter, a second transverse midline a second minimum width line, and an incontinence absorbent layer having an incontinence absorbent shape, the perimeter defining a second article shape and a second article size, wherein the first article shape is substantially the same as the second article shape, and wherein the first article size is substantially the same as the second article size.

9 Claims, 1 Drawing Sheet

(56) References Cited

U.S. PATENT DOCUMENTS

| | | |
|---|---|---|
| 6,908,456 B1 | 6/2005 | Drevik |
| 6,921,392 B1 | 7/2005 | Drevik et al. |
| D510,434 S | 10/2005 | Carlucci et al. |
| 6,972,010 B2 | 12/2005 | Pesce et al. |
| D554,254 S | 10/2007 | Cole |
| D592,743 S | 5/2009 | Moennig |
| D626,218 S | 10/2010 | Lundin |
| 7,947,864 B2 | 5/2011 | Damay et al. |
| 8,246,593 B2 | 8/2012 | Lavash |
| 2003/0065299 A1 | 4/2003 | Carlucci et al. |
| 2003/0097111 A1 | 5/2003 | Lundin |
| 2005/0192549 A1 | 9/2005 | Veglio et al. |
| 2006/0129115 A1* | 6/2006 | Visscher et al. ............... 604/361 |
| 2007/0225669 A1 | 9/2007 | Dyer |
| 2008/0294139 A1 | 11/2008 | Ecker et al. |
| 2008/0294140 A1 | 11/2008 | Ecker et al. |
| 2009/0012491 A1 | 1/2009 | D'Addario et al. |
| 2010/0082003 A1 | 4/2010 | Hunter et al. |
| 2012/0259306 A1 | 10/2012 | Petersen |

\* cited by examiner

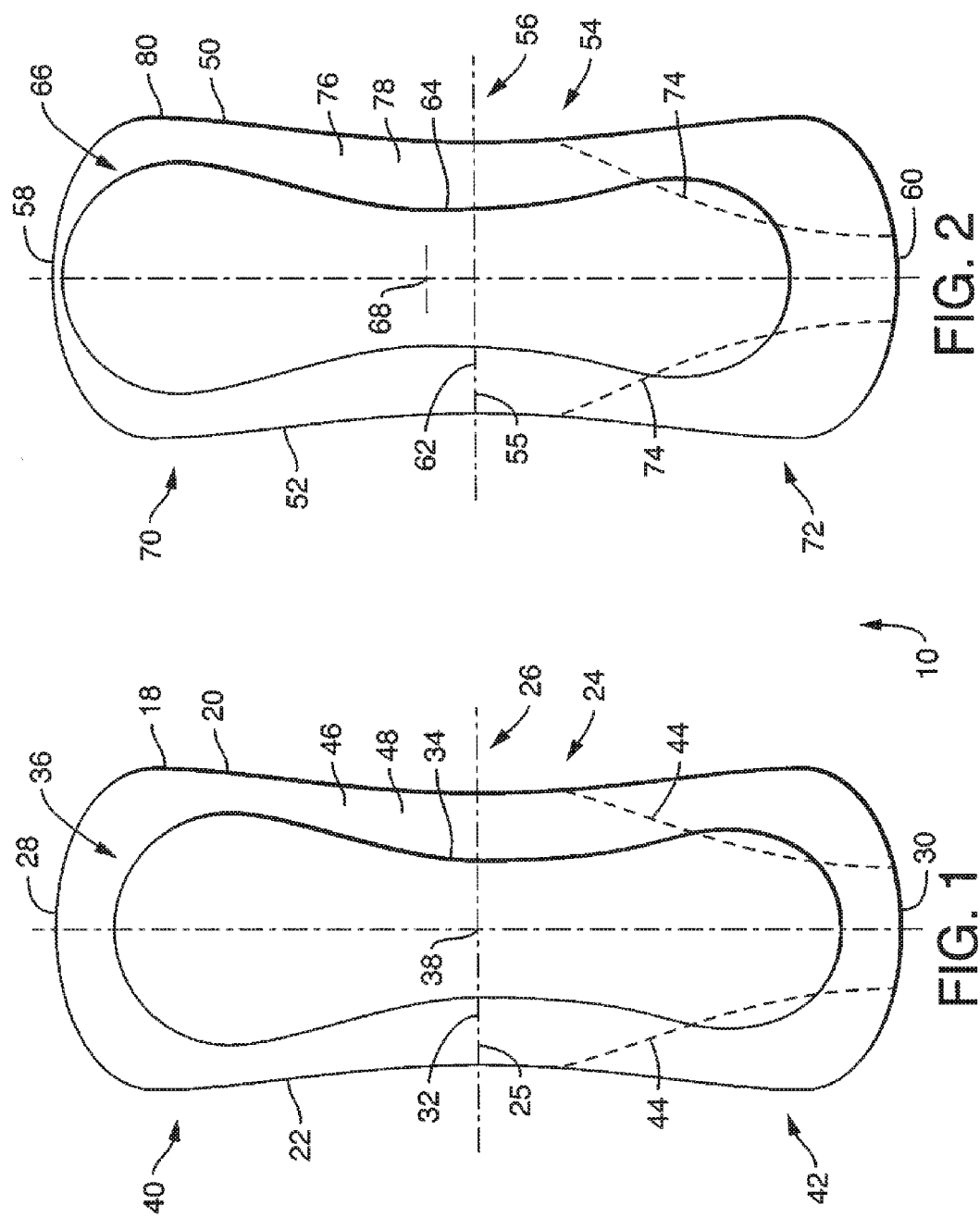

TRANSITIONAL ABSORBENT PAD AND PANTILINER

BACKGROUND

The present disclosure concerns personal hygiene products, more particularly, disposable absorbent articles made to protect a user's underwear from staining. Disposable absorbent articles such as liners are a class of absorbent articles (e.g., most often referred to as pantiliners for feminine use) designed to absorb small amounts of body fluids. They are smaller and more compact than conventional feminine sanitary napkins or pads. These products are designed to be flexible and soft and to protect the underwear of the user from staining. Disposable absorbent articles can be shaped as an elongated oval, and are intended to cover the underwear in the perineal area of the user, i.e., the crotch portion of the underwear.

Many women start using menstrual liners and pads to manage their light incontinence (light bladder leakage). At some point they are aware that their incontinence needs are not being met by their menstrual liner or pad. When they discover this incontinence need, they begin to look for a targeted incontinence disposable absorbent article. When they make the transition, they want the incontinence disposable absorbent article to address incontinence without giving up the comfort of their menstrual liner or pad.

The problem is designing a transition incontinence disposable absorbent article that provides superior urine leakage protection while giving the feel and look of a menstrual liner or pad by having both actual and perceived comfort of a menstrual liner or pad. An incontinence disposable absorbent article needs to contain typically drips and dribbles of urine. Many women initially use menstrual liners and pads to manage their incontinence needs. Menstrual liners and pads are designed to capture vaginal fluids and menses that exit from the vagina, while incontinence disposable absorbent articles are designed to capture urine that exits from the urethra. Because the urethral opening is positioned forward of or in the anterior direction from the vaginal opening, the insult zone of the absorbent of an incontinence disposable absorbent article needs to be forward of the insult zone of the menstrual pad.

In addition, the sides of the incontinence disposable absorbent article need to deliver the actual and perceived comfort of a traditional menstrual pad or liner.

SUMMARY

The solution is a transitional incontinence disposable absorbent article that has both the perceived and actual comfort of a woman's menstrual liner or pad while providing superior urine leakage protection. Typically, two approaches have been tried: 1) modify a traditional menstrual pad or liner by placing more superabsorbent in the pad or liner, and 2) modify a traditional incontinence disposable absorbent article by giving it the overall size and shape of a menstrual pad or liner. Both of these solutions provide an incontinence disposable absorbent article that is more expensive than a menstrual pad or liner and is generally over-designed for its need.

What is needed is an incontinence disposable absorbent article that synergistically combines the absorbency characteristics of a traditional incontinence disposable absorbent article with feel and look of a menstrual pad or liner without any added cost. This can be accomplished with an incontinence disposable absorbent article that has the overall shape of a menstrual liner and pad with most of the absorbency shifted to where it is needed. In response to the discussed difficulties and problems encountered in the art, a new disposable absorbent article has been developed for everyday use that provides light absorbency protection without sacrificing comfort. The purposes and features of the present disclosure will be set forth in and are apparent from the description that follows, as well as will be learned by practice of the disclosure. Additional features of the disclosure will be realized and attained by the product and process particularly pointed out in the written description and claims hereof, as well as from the appended drawings.

In one aspect, the disclosure provides an array of personal care absorbent articles, the array including a menstrual absorbent article having a perimeter, a first transverse midline, a first minimum width line, and a menstrual absorbent layer having a menstrual absorbent shape, the perimeter defining a first article shape and a first article size. The array also includes an incontinence absorbent article having a perimeter, a second transverse midline a second minimum width line, and an incontinence absorbent layer having an incontinence absorbent shape, the perimeter defining a second article shape and a second article size, wherein the first article shape is substantially the same as the second article shape, and wherein the first article size is substantially the same as the second article size.

In another aspect, the disclosure provides an array of personal care absorbent articles, the array including a menstrual absorbent article having a perimeter, a first transverse midline, a first minimum width line, and a menstrual absorbent layer having a menstrual absorbent shape, the perimeter defining a first article shape and a first article size. The array also includes an incontinence absorbent article having a perimeter, a second transverse midline a second minimum width line, and an incontinence absorbent layer having an incontinence absorbent shape, the perimeter defining a second article shape and a second article size, wherein the first article shape is substantially the same as the second article shape, wherein the first article size is substantially the same as the second article size, and wherein the menstrual absorbent shape is different from the incontinence absorbent shape In still another aspect, the disclosure provides an array of personal care absorbent articles, the array including a menstrual absorbent article having a perimeter, a first transverse midline, a first minimum width line, and a menstrual absorbent layer having a menstrual absorbent shape and a first center of mass, the perimeter defining a first article shape and a first article size. The array also includes an incontinence absorbent article having a perimeter, a second transverse midline a second minimum width line, and an incontinence absorbent layer having an incontinence absorbent shape and a second center of mass, the perimeter defining a second article shape and a second article size, wherein the first article shape is substantially the same as the second article shape, wherein the first article size is substantially the same as the second article size, and wherein the distance between the second center of mass and the second transverse midline is greater than the distance from the first center of mass to the first transverse midline.

It is to be understood that both the foregoing general description and the following detailed description are exemplary and are intended to provide further explanation of the disclosure claimed. The accompanying drawings, which are incorporated in and constitute part of this specification, are included to illustrate and provide a further understanding of the disposable absorbent articles of the disclosure.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

FIG. 1 is a plan view of a menstrual absorbent article of the present disclosure having an hourglass shape; and FIG. 2 is a plan view of an incontinence absorbent article of the present disclosure, in an array with the menstrual absorbent article of FIG. 1, with an absorbent layer offset from the absorbent layer of FIG. 1.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

As used herein, "disposable" means being disposed of after a single use and not intended to be washed and reused.

As used herein, "layer" means a mass of fibers or material having sufficient bonded integrity between the fibers or material to be maintained in a substantially coherent sheet when the sheet is used for its intended purpose.

As used herein, "hydrophilic" means fibers or surfaces of fibers that are wetted by aqueous liquids in contact with the fibers. The degree of wetting of the materials can be described in terms of contact angles and the surface tensions of the liquids and materials involved. Equipment and techniques suitable for measuring the wettability of particular fiber materials or blends of fiber materials can be provided by a Cahn SFA-222 Surface Force Analyzer System. When measured with this system, fibers having contact angles less than 90 degrees are designated "wettable," i.e., hydrophilic, and fibers having contact angles greater than 90 degrees are "non-wettable," i.e., hydrophobic.

As used herein, "hydrophobic" means fibers or surfaces of fibers that are not hydrophilic.

As used herein the term "nonwoven" means a layer of material having a structure of individual fibers or threads that are interlaid together, but not in an identifiable manner like a knitted fabric is so constructed. Nonwoven materials or layers have been formed from many processes such as for example, meltblowing processes, spunbonding processes, and bonded carded web processes. The basis weight of nonwoven material is usually expressed in ounces of material per square yard (osy) or grams per square meter (gsm) and the fiber diameters useful are usually expressed in microns (i.e., note that to convert from osy to gsm, multiply osy by 33.91).

As used herein the term "microfiber(s)" means small diameter fiber(s) having an average diameter not greater than about 75 microns, for example, having an average diameter of from about 0.5 microns to about 50 microns, or more particularly, microfibers can have an average diameter of from about 2 microns to about 40 microns. Another frequently used expression of fiber diameter is denier, which is defined as grams per 9000 meters of a fiber and can be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns can be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex can be calculated as denier/9.

"Bonded carded" refers to material or layers that are made from staple fibers that are sent through a combing or carding unit, which separates or breaks apart and aligns the staple fibers in the machine direction to form a generally machine direction-oriented fibrous nonwoven layer. This material can be bonded together to form a nonwoven layer by methods that include, without limitation, mechanical bonding such as needle punching, hydroentangling, and stitch bonding.

FIGS. 1 and 2 illustrate disposable absorbent articles 20, 50 of the present disclosure in the form of a liner or pad. The disposable absorbent articles 20, 50 are typically configured for use in a crotch portion of underwear. The disposable absorbent articles 20, 50 include a cover layer 46, 76 having a top surface 48, 78 and an opposite bottom surface (not shown). The disposable absorbent articles 20, 50 also include a baffle layer 18, 80 in facing relationship to the cover layer 46, 76 and attached thereto by any suitable means. The disposable absorbent articles 20, 50 can also include an absorbent layer 34, 64 disposed between the cover layer 46, 76 and the baffle layer 18, 80.

The cover layer 46, 76 can be manufactured from any suitable material including a mixture of hydrophilic microfibers and hydrophobic microfibers, where a quantity of the hydrophilic microfibers and the hydrophobic microfibers are located at the top surface 48, 78 but a larger quantity of hydrophobic microfibers are located at the top surface 48, 78 than are a quantity of hydrophilic microfibers located at the top surface 48, 78 based on a total weight of the mixture of microfibers in the cover layer 46, 76.

Such a cover layer 46, 76 can be advantageous for light menstrual use or for delivery of medicaments. More sophisticated types of cover layers can incorporate treatments of lotions or medicaments to improve the environment near the skin or to actually improve skin health. Such treatments include aloe, vitamin E, baking soda, and other preparations as might be known or developed by those skilled in the art.

The hydrophilic microfibers and hydrophobic microfibers can be either synthetic fibers or natural fibers, as long as they have the desired wettability or nonwettability, and the cover layer 46, 76 can be formed as a bonded carded layer. Synthetic fibers include those made from polyolefins, polyamides, polyesters, rayon, acrylics, superabsorbents, LYOCELL® regenerated cellulose, and any other suitable synthetic fibers known to those skilled in the art. Many polyolefins are available for fiber production, including polyethylenes such as Dow Chemical's ASPUN® 6811A low density polyethylene. 2553 LLDPE, 25355, and 12350 high density polyethylene are such suitable polymers. These polyethylenes have melt flow rates, respectively, of about 26, 40, 25, and 12. Fiber-forming polypropylenes include Exxon Chemical Company's ESCORENE® PD 3445 polypropylene and Montell Chemical Co.'s PF304. Other polyolefins are also available.

Natural fibers can include wool, cotton, flax, hemp and wood pulp. Wood pulps include standard softwood fluffing grade such as CR-1654 (US Alliance Pulp Mills, Coosa, Ala.). Pulp can be modified to enhance the inherent characteristics of the fibers and their processability. Crimping can be imparted to the fibers, e.g., by conventional means. Curl can be imparted to the fibers, e.g., by methods including chemical treatment or mechanical twisting. Curl is typically imparted before crosslinking or stiffening. Pulps can be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid, or other polycarboxylic acids. Some of these agents are less preferable than others due to environmental and health concerns. Pulp can also be stiffened by the use of heat or caustic treatments such as mercerization. Examples of these types of fibers include NHB416, which is a chemically crosslinked southern softwood pulp fibers that enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc. of Memphis, Tenn., has a chemical treatment that sets in a curl and twist, in addition to imparting added dry and wet stiffness and resilience to the fiber. Other suitable pulps are Buckeye HP2 pulp and IP Supersoft from International Paper Corporation. Suitable rayon fibers are 1.5 denier Merge 18453 fibers from Acordis Cellulose Fibers Incorporated of Axis, Ala.

The disposable absorbent articles 20, 50 also include a liquid-impervious baffle layer 18, 80 having a top surface 48, 78 and an opposite bottom surface (not shown). The baffle layer 18, 80 is disposed between the cover layer 46, 76 and a backing layer (if present). The top surface 48, 78 of the baffle layer 18, 80 can be secured to the bottom surface of the cover layer 46, 76 or there can be one or more additional layers or materials therebetween.

The baffle layer 18, 80 is impermeable to liquid to keep the clothing or underwear of the wearer from becoming soiled. The impermeable baffle layer 18, 80 is preferably made from a thin film and is generally made from plastic though other materials can be used. Nonwovens, films, or film-coated nonwovens can be used as the baffle layer 18, 80 as well. Suitable film compositions for the baffle layer 18, 80 include polyethylene film that can have an initial thickness of from about 0.5 mil (0.012 millimeter) to about 5.0 mil (0.12 millimeter). The baffle layer 18, 80 can optionally be composed of a vapor- or gas-permeable, microporous "breathable" material that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. A greater the degree of breathability is generally obtained with more filler and a higher degree of stretching. Other suitable thermoplastic materials such as other olefins, nylons, polyesters or copolymers of, such as polyethylene and polypropylene, can also be used.

Adhesive (not shown) or other similarly-functioning materials for attaching the disposable absorbent articles 20, 50 to underwear can be applied to at least a portion of the bottom surface of the baffle layer 18, 80 to keep the disposable absorbent articles 20, 50 in place while in use. The adhesive can be applied in any effective pattern. The adhesive can, for example, be applied as a narrow strip down the center of the disposable absorbent articles 20, 50, a wide strip covering the disposable absorbent articles 20, 50 in a rectangular shape with a width equal to the width of the disposable absorbent articles 20, 50 at their narrowest points, or can cover the entire backing layer. A narrower strip of adhesive is advisable for more breathable aspects because the adhesive tends to detract from breathability.

The disposable absorbent articles 20, 50 can also include a removable backing layer (not shown). Alternatively or additionally, the backing layer can be removably secured to the bottom surface of the baffle layer 18, 80 or there can be one or more additional layers or materials therebetween. The removable backing layer, such as peelable or detachable paper, is applied to the adhesive on the bottom surface of the baffle layer 18, 80. If the adhesive is applied as a narrow strip in the center of the disposable absorbent articles 20, 50, additional adhesive can be applied to the backing layer in other areas. The backing layer is removed from the adhesive by the user prior to application of the disposable absorbent articles 20, 50 to the underwear.

The disposable absorbent articles 20, 50 can further include an absorbent layer 34, 64. The absorbent layer 34, 64 can include a coform material, a resilient coform material, or an airlaid material, each of which can further include a superabsorbent material. The presence and amount of superabsorbent material depends on the application of the absorbent layer 34, 64 and the desired absorbent capacity. The absorbent layer 34, 64 can instead or additionally include a high-density, hydrogen-bonded, fluff/superabsorbent polymer material, a spunlace material, a superabsorbent polymer/adhesive composite material, a foam material, or any combination thereof. Any of these absorbent layer materials can further include fluff pulp.

Various other layers (not shown) can be included in disposable absorbent articles 20, 50 of this disclosure provided the desired feature(s) of the disclosure can still be obtained. Such other layers can be surge layers, and can be placed between the cover layer 46, 76 and the baffle layer 18, 80 and are designed, as the name suggests, to contain surges of liquid so that the absorbent layer 34, 64 can absorb the amount of liquid more evenly over time. Distribution layers can also be included in the article. Distribution layers can be located next to the absorbent layer 34, 64 and accept liquid from the surge layer and distribute it to other areas of the absorbent layer 34, 64. In this manner, rather than absorbing liquid exclusively in the vicinity of initial impact upon the cover layer 46, 76, more of the absorbent layer 34, 64 is used throughout the disposable absorbent articles 20, 50.

More specifically, a transitional incontinence disposable absorbent article 50 that synergistically combines the absorbency characteristics of a traditional incontinence disposable absorbent article with the feel and look of a menstrual pad or liner provides the comfort and value necessary when arrayed with a menstrual liner to transition a woman from the menstrual liner to a standard incontinence liner or pad.

Menstrual liners and pads are designed to capture vaginal fluids and menses that exit from the vagina, while incontinence liners and pads are designed to capture urine that exits from the urethra. Because the urethral opening is positioned forward of or in the anterior direction from the vaginal opening, the insult zone of the absorbent layer of an incontinence disposable absorbent article needs to be forward of the insult zone of the menstrual pad. As a result, the transitional incontinence disposable absorbent article 50 has the overall shape of a menstrual disposable absorbent article 20 with absorbency shifted to where it is needed.

A woman's transition to an incontinence liner or pad is facilitated by providing an array 10 of personal care disposable absorbent articles 20, 50. The array 10 includes a menstrual absorbent article 20 such as a menstrual liner or pantiliner. The menstrual absorbent article 20 has a perimeter 22 that is the outline of the menstrual absorbent article 20, or the shape of the menstrual absorbent article 20 when viewed in a plan view. The perimeter 22 defines a menstrual article shape 24 and a menstrual article size 26. The menstrual article shape can be any suitable shape including round, oval, hourglass, dog bone, elongate, rectilinear, etc. The menstrual article shape 24 can also be symmetric or asymmetric, particularly with respect to a transverse midline 25. The menstrual article shape 24 can be configured in any suitable manner to accommodate fit and flexibility.

The menstrual absorbent article 20 also has a first transverse midline 25 equidistant from the anterior end 28 and the posterior end 30 of the menstrual absorbent article 20. The menstrual absorbent article 20 also has a minimum width line 32, which is the transverse line taken at the point of minimum width of the menstrual absorbent article 20.

The menstrual absorbent article 20 further includes a menstrual absorbent layer 34. The menstrual absorbent layer 34 has a menstrual absorbent shape 36, which is the shape of the menstrual absorbent layer 34 when viewed in a plan view. The menstrual absorbent shape 36 can be any suitable shape including round, oval, hourglass, dog bone, elongate, rectilinear, etc. The menstrual absorbent shape 36 can also be symmetric or asymmetric, particularly with respect to the transverse midline 25. The menstrual absorbent shape 36 can be configured in any suitable manner to accommodate fit and flexibility, and need not be similar in shape to the menstrual article shape 24.

The array 10 also includes an incontinence absorbent article 50 such as an incontinence liner or pantiliner. The incontinence absorbent article 50 has a perimeter 52 that is the outline of the incontinence absorbent article 50, or the shape of the incontinence absorbent article 50 when viewed in a plan view. The perimeter 52 defines an incontinence article shape 54 and an incontinence article size 56. The incontinence article shape 54 can be any suitable shape including round, oval, hourglass, dog bone, elongate, rectilinear, etc. The incontinence article shape 54 can also be symmetric or asymmetric, particularly with respect to a transverse midline 55. The incontinence article shape 54 can be configured in any suitable manner to accommodate fit and flexibility.

The incontinence absorbent article 50 also has a first transverse midline 55 equidistant from the anterior end 58 and the posterior end 60 of the incontinence absorbent article 50. The incontinence absorbent article 50 also has a minimum width line 62, which is the transverse line taken at the point of minimum width of the incontinence absorbent article 50.

The incontinence absorbent article 50 further includes an incontinence absorbent layer 64. The incontinence absorbent layer 64 has an incontinence absorbent shape 66, which is the shape of the incontinence absorbent layer 64 when viewed in a plan view. The incontinence absorbent shape 66 can be any suitable shape including round, oval, hourglass, dog bone, elongate, rectilinear, etc. The incontinence absorbent shape 66 can also be symmetric or asymmetric, particularly with respect to the transverse midline 55. The incontinence absorbent shape 66 can be configured in any suitable manner to accommodate fit and flexibility, and need not be similar in shape to the incontinence article shape 54.

To facilitate transition, the shape 24 of the menstrual absorbent article 20 is preferably substantially the same as the shape 54 of the incontinence absorbent article 50. In addition, the transition can be further facilitated by having the size 26 of the menstrual absorbent article 20 be substantially the same as the size 56 of the incontinence absorbent article 50. The shape 36 of the menstrual absorbent layer 34 can be substantially the same as the shape 66 of the incontinence absorbent layer 64, or the shape 36 of the menstrual absorbent layer 34 can be different from the shape 66 of the incontinence absorbent layer 64. The menstrual absorbent layer 34 and the incontinence absorbent layer 64 can be of any suitable shape.

The menstrual absorbent layer 34 also includes a center of mass 38. In most cases in which the menstrual absorbent layer 34 is not a zoned absorbent layer, the center of mass 38 will be essentially the same as the geographical center of the menstrual absorbent layer 34. In addition, the incontinence absorbent layer 64 also includes a center of mass 68. In most cases in which the incontinence absorbent layer 64 is not a zoned absorbent layer, the center of mass 68 will be essentially the same as the geographical center of the incontinence absorbent layer 64.

In one aspect of the present disclosure, the distance between the center of mass 68 of the incontinence absorbent layer 64 and the transverse midline 55 of the incontinence absorbent article 50 is greater than the distance from the center of mass 38 of the menstrual absorbent layer 34 to the transverse midline 25 of the menstrual absorbent article 20.

In another aspect of the present disclosure, the distance between the center of mass 68 of the incontinence absorbent layer 64 and the minimum width line 62 of the incontinence absorbent article 50 is greater than the distance from the center of mass 38 of the menstrual absorbent layer 34 to the minimum width line 32 of the menstrual absorbent article 20.

The menstrual absorbent article 20 includes an anterior zone 40 and a posterior zone 42. The incontinence absorbent article 50 also includes an anterior zone 70 and a posterior zone 72. In one aspect of the present disclosure, the posterior zone 42 of the menstrual absorbent article 20 includes one or more fold lines 44. In another aspect of the present disclosure, the posterior zone 72 of the incontinence absorbent article 50 includes one or more fold lines 74.

The instant disclosure also includes a convertible, disposable absorbent article that can be used with conventional underwear or with thong style panties or underwear. The disposable absorbent articles 20, 50, as shown in FIGS. 1 and 2, have a slightly "hourglass" shape. The disposable absorbent articles 20, 50 optionally have a single line of embossing 44, 74 corresponding approximately to the shape of a thong panty that is used for folding the disposable absorbent articles 20, 50 and that defines three separate areas of the disposable absorbent articles 20, 50. The central areas are in absorbent service when the disposable absorbent articles 20, 50 are applied to either style of panty. The periphery includes side areas that are in absorbent service when the disposable absorbent articles 20, 50 are applied to a conventional, hourglass-shaped panty but are folded under the panty along the fold (embossing) lines 44, 74 when used with a thong panty. It is possible to have additional lines of embossing for folding on either side of the lines 44, 74 shown in FIGS. 1 and 2, and attention is directed to a pending application of the assignee of the present application, titled "DUAL-USE PANTILINER" and published Jun. 20, 2002 as WO 02/47596.

All publications, patents, and patent documents cited in the specification are incorporated by reference herein, as though individually incorporated by reference. In the case of any inconsistencies, the present disclosure, including any definitions herein, will prevail. While the invention has been described in detail with respect to the specific aspects thereof, it will be appreciated that those skilled in the art, upon attaining an understanding of the foregoing, can readily conceive of alterations to, variations of, and equivalents to these aspects that fall within the spirit and scope of the present disclosure, that should be assessed accordingly to that of the appended claims.

What is claimed is:

1. An array of personal care absorbent articles, the array comprising:
   a menstrual absorbent article having a perimeter, a first transverse midline, a first minimum width line, and a menstrual absorbent layer having a menstrual absorbent shape and a first center of mass, the perimeter refining a first article shape and a first article size; and
   an incontinence absorbent article having a perimeter, a second transverse midline a second minimum width line, and an incontinence absorbent layer having an incontinence absorbent shape and a second center of mass, the perimeter defining a second article shape and a second article size,
   wherein the first article shape is substantially the same as the second article shape, wherein the first article size is substantially the same as the second article size, and wherein the distance between the second center of mass and the second transverse midline is greater than the distance from the first center of mass to the first transverse midline.

2. The array of claim 1, wherein the distance between the second center of mass and the second minimum width line is greater than the distance from the first center amass to the first minimum width line.

3. The array of claim 1, wherein one of the menstrual absorbent layer and the incontinence absorbent layer includes superabsorbent material.

4. The array of claim 3, wherein the incontinence absorbent layer includes superabsorbent material.

5. The array of claim 1, wherein the menstrual absorbent layer is free of superabsorbent material.

6. The array of claim 1, wherein the menstrual absorbent layer has a structure different from the structure of the incontinence absorbent layer.

7. The array of claim 1, wherein the position of the incontinence absorbent layer with respect to the second transverse midline is offset when compared to the position of the menstrual absorbent layer with respect to the first transverse midline.

8. The array of claim 1, wherein the menstrual absorbent article and the incontinence absorbent article each includes an anterior zone and a posterior zone, and wherein each posterior zone includes a fold line.

9. The array of claim 8, wherein each posterior zone includes a plurality of fold lines.

* * * * *